(12) United States Patent
Cheung et al.

(10) Patent No.: US 7,511,004 B2
(45) Date of Patent: Mar. 31, 2009

(54) LAVATORY BLOCK COMPOSITIONS

(75) Inventors: Tak Wai Cheung, Yuma, AZ (US); Edward Fu, Montvale, NJ (US); Tri Nguyen, Succasunna, NJ (US); Steven Wu, Montvale, NJ (US)

(73) Assignee: Reckitt Benckiser Inc., Parsippany, NJ (US)

( * ) Notice: Subject to any disclaimer, the term of this patent is extended or adjusted under 35 U.S.C. 154(b) by 0 days.

(21) Appl. No.: 11/917,306

(22) PCT Filed: May 23, 2006

(86) PCT No.: PCT/GB2006/001892

§ 371 (c)(1),
(2), (4) Date: Mar. 10, 2008

(87) PCT Pub. No.: WO2006/136773

PCT Pub. Date: Dec. 28, 2006

(65) Prior Publication Data

US 2008/0194448 A1    Aug. 14, 2008

Related U.S. Application Data

(60) Provisional application No. 60/692,992, filed on Jun. 22, 2005.

(30) Foreign Application Priority Data

Oct. 17, 2005 (GB) .................................. 0520990.3

(51) Int. Cl.
| | |
|---|---|
| *C11D 1/12* | (2006.01) |
| *C11D 3/395* | (2006.01) |
| *C11D 9/24* | (2006.01) |
| *C11D 17/00* | (2006.01) |

(52) U.S. Cl. ...................... 510/192; 510/367; 510/440; 510/445; 510/492; 510/502

(58) Field of Classification Search ................ 510/192, 510/367, 440, 445, 492, 502
See application file for complete search history.

(56) References Cited

U.S. PATENT DOCUMENTS

| 4,578,207 A | 3/1986 | Holdt et al. |
| 5,939,372 A | 8/1999 | Schmid et al. |

FOREIGN PATENT DOCUMENTS

| GB | 1194745 A | | 6/1970 |
| GB | 1403472 A | | 12/2007 |
| WO | WO 03/042462 | * | 5/2003 |

* cited by examiner

*Primary Examiner*—Brian P Mruk
(74) *Attorney, Agent, or Firm*—Norris McLaughlin & Marcus, PA

(57) ABSTRACT

Improved treatment blocks useful in the treatment of lavatory appliances, particularly toilets are provided. The improved treatment blocks are solid block compositions which provide an extended service life, particularly when used in an ITB device. Methods of producing the solid block composition and treatment blocks therefrom, as well as methods of use are also disclosed.

21 Claims, No Drawings

LAVATORY BLOCK COMPOSITIONS

This is an application filed under 35 USC 371 of PCT/GB2006/001892.

The present invention relates to improved solid treatment block compositions useful for providing an active treatment composition to a sanitary appliance, e.g., a toilet or urinal. More specifically the present invention relates to improved solid block cleaning compositions having increased service life when used for such purposes.

Solid treatment blocks have found widespread use in the cleaning and/or disinfecting treatment of sanitary appliances as, once installed they require little or no user intervention during their effective service life. Such solid treatment block compositions are considered to operate in an automatic fashion and their effective functioning is dependent in great part upon their composition, their dissolution characteristics when contacted with water and their placement within the sanitary appliance which they are used to treat. Typically such solid treatment block compositions are used in either one of two modes, either as an "ITC" or "in the cistern" mode, or as an "ITB" or "in the bowl" mode. In the former the solid treatment block composition is placed in water supply tank, also known as the cistern or toilet tank wherein it is expected to dissolve over a period of time and thus deliver active cleaning and/or disinfecting constituents to the water present in the cistern which is periodically used to flush the toilet bowl or other sanitary appliance, e.g., a urinal. Such a solid treatment block composition may be supplied to the interior of the cistern as a tablet or other self supporting shape, or alternately the solid treatment block composition may be provided in a container or cage, or as part of a dispensing device, from which the active cleaning and/or disinfecting constituents are delivered to the water present in the cistern. In the latter, the solid treatment block composition is placed within the bowl, typically supported by a device, cage, or even a simple bent wire such that the active cleaning and/or disinfecting constituents are contacted with water flushed into the sanitary appliance, especially the bowl of a toilet, or the interior of a urinal. In such an installation it is expected that a part of the solid treatment block composition is dissolved with each flush of water passing though the device such that an amount of active cleaning and/or disinfecting constituents are dispensed to the toilet bowl, urinal, etc.

The art is replete with many forms of solid treatment block compositions which find use either as ITB or ITC type compositions. Examples of such solid treatment block compositions include those described in the following: U.S. Pat. Nos. 4,246,129 4,269,723; 4,043,931; 4,460,490; 4,722,802; 4,820,449; 5,342,550; 5,562,850; 5,711,920; 5,759,974; 5,939,372; 6,001,789 as well as U.S. Pat. No. 6,294,510. Each of these patents disclosed solid treatment block compositions which provide specific technical benefits, or overcome specific technical shortcomings which were hithero known to the art until the time of the respective invention. For example, various processing shortcomings are known from the manufacture of such blocks, or from the dissolution characteristics of such blocks as are described in these patents or which are otherwise known to the relevant art.

Thus, while these known-art solid treatment block compositions are useful and provide certain advantageous features there is nonetheless a real and continuing need in the art for further solid treatment block compositions which are effective in the treatment of sanitary appliances both in an ITB and/or in an ITC mode. There also remains a real and urgent need in the art for such improved solid treatment block compositions which provide improved service life, particularly when used within a device such as in an ITB or ITC device installed in a toilet or other sanitary appliance.

Accordingly it is an object of the present invention to provide an improved solid treatment block composition useful as an ITB or ITC device installed in a toilet or other sanitary appliance. Such a solid treatment block composition operates to provide a cleaning effect to sanitary appliances within which they are used.

A further object of the present invention to provide an improved solid treatment block composition useful as an ITB or ITC device installed in a toilet or other sanitary appliance. Such a solid treatment block composition operates to provide a cleaning and bleaching effect (preferably both cleaning and bleaching effect) to sanitary appliances within which they are used.

It is a further object of the invention to provide improved processes for the manufacture of the aforesaid solid treatment block compositions.

It is a yet further object of the invention which exhibits improved handling characteristics subsequent to the manufacture of the aforesaid solid treatment block compositions, especially prior to their use of solid blocks formed therefrom as an ITB or ITC device installed in a toilet or other sanitary appliance.

It is a still further object of the invention to provide an improved solid treatment block composition useful in an ITB or ITC device in the form of a solid, self-supporting block installed in a toilet or other sanitary appliance which exhibits good delivery characteristics and is useful over a longer term than known art block compositions.

It is yet further object of the invention to provide an improved solid treatment block which is particularly useful in an ITB or ITC device which exhibits an increased service life.

It is as still further object of the invention to provide improved solid treatment blocks particularly useful in an ITB or ITC device which exhibits a high ratio of surface area to block volume, and which exhibits a long service life when used in such a device.

These and other objects of the invention will become apparent to those of ordinary skill in this art from the following detailed description.

In one aspect of the invention there is provided an improved treatment block which exhibits good delivery characteristics and dimensional stability during their use in providing a cleaning and/or disinfecting or sanitizing treatment of a lavatory appliance within which they are used.

In a further aspect of the invention there is provided an improved treatment block according to the first or second aspects of the invention as recited above which provide improved manufacturing characteristics particularly improved extrusion characteristics and/or improved handling characteristics of treatment blocks formed from the solid block composition subsequent to their manufacture but prior to their use in a sanitary appliance.

According to a yet further aspect of the invention there are provided solid treatment blocks formed from a solid block composition which comprises:

10-40% wt., preferably 15-35% wt. of a linear alkyl benzene sulfonate surfactant, preferably a dodecylbenzene sulfonate anionic surfactant;

8-40% wt., preferably 9-55% wt. of an alpha olefin sulfonate anionic surfactant;

10-40% wt., preferably 10-35% wt. of one or more mono- or di-alkanol amides derived from $C_8$-$C_{16}$ fatty acids, especially $C_{12}$-$C_{14}$ fatty acids having a $C_2$-$C_6$ monoamine or diamine moiety preferably a linear monoethanol amide;

5-30% wt., preferably 15-25% wt. of a diluent material, preferably sodium sulfate;

0.1-15% wt., preferably 0.5-5% wt. of a filler material, preferably silica;

0.05-7% wt., preferably 1-3.5% wt of a bleach constituent;

optionally but preferably a hydrocarbon solvent constituent;

optionally but preferably a film forming polymer constituent;

optionally to 40% wt. further additive constituents, including but not limited to further detersive cosurfactants, fillers, binders, fragrances, processing aids such as lubricants and tabletting aids, bleaches, sanitizing compositions and the like. In particularly preferred embodiments the solid treatment blocks exhibit a long service life when mounted in the devices described herein, which service life is believed to be superior to many known art ITB lavatory cleaning block compositions. The aforesaid solid treatment blocks find particular use as ITB or ITC lavatory cleaning block compositions.

According to a second aspect of the invention there is provided a solid treatment block formed from a solid block composition as recited above wherein the ratio of block volume to block surface area is at least about 0.25, preferably at least about 0.27, more preferably is at least about 0.29, and still more preferably is at least bout 0.30.

According to a third aspect of the invention there is provided a solid treatment block as recited above wherein the block composition loses not more than 50%, preferably not more than 20%, more preferably not more than 10% of its initial weight subsequent to 100 flush cycles when the block has been suspended in an ITB device in the path of flush water released from the cistern during each flush cycle.

According to a fourth aspect of the invention there is provided a solid treatment block as recited above wherein the block composition increases above its initial weight subsequent to 100 flush cycles when the block has been suspended in an ITB device in the path of flush water released from the cistern during each flush cycle.

The solid block composition of the invention necessarily comprises anionic surfactants. Preferably these anionic surfactants are those whose melting points are sufficiently high, above about 110° F., preferably above 125° F., to permit processing according to known art techniques. However, small amounts of low melting point surfactants and even liquid surfactants may be used in providing the surfactant constituent.

The compositions necessarily comprise one or more linear alkyl benzene sulfonate surfactants wherein the alkyl portion contains 8 to 16 carbon atoms, and most preferably about 11 to 13 carbon atoms. According to particularly preferred embodiments of the invention, the solid block compositions necessarily include an anionic surfactant, especially linear alkyl benzene sulfonates containing 11, 12 or 13 carbon atoms, as well as salt forms thereof. These are necessarily present in an amount of 10-40% wt., preferably 15-35% wt. based on the total weight of the block composition of which they form a part.

The compositions necessarily comprise one or more alkyl olefin sulfonates surfactants wherein the alkyl portion contains 8 to 24 carbon atoms, preferably from 10 to 18 carbon atoms. Especially preferred are alkali metal salts, e.g. sodium or potassium salts of one or more $C_{12}$, $C_{14}$ and $C_{16}$ sulfonates. These are necessarily present in amounts of 8-40% wt., preferably 9-35% wt. based on the total weight of the block composition of which they form a part.

Particularly preferred weight percentages of the essential anionic surfactants are disclosed with reference to one or more of the Examples described hereinafter.

According to certain particularly preferred embodiments the sole anionic surfactants present are at least one linear alkyl benzene sulfonate and at least one alkyl olefin sulfonate, e.g, $C_{12}$, $C_{14}$ and $C_{16}$ sulfonates.

According to further particularly preferred embodiments the sole surfactant constituents in the inventive compositions are at least one linear alkyl benzene sulfonate and at least one alkyl olefin sulfonate, e.g., $C_{12}$, $C_{14}$ and $C_{16}$ sulfonates.

The inventors have surprisingly found that treatment blocks formed with even the reduced amounts of essential anionic surfactants, and in the absence of cosurfactants still provide a treatment block with good detersive properties and a surprisingly long service life.

The inventors have also noted that with the reduction of

The inventive compositions further necessarily comprise 10-40% wt., preferably 10-35% wt. of one or more mono- or di-alkanol amides derived from $C_8$-$C_{16}$ fatty acids; these materials provide a degree of hydrophobicity to the treatment blocks formed from the solid block composition whose presence in the treatment blocks contributes to the slow uniform dissolution of the treatment blocks when contacted with water, and simultaneously the controlled release of the active constituents of the solid block composition. Preferred for use as the dissolution control agents are mono- or di-alkanol amides derived from $C_8$-$C_{16}$ fatty acids, especially $C_{12}$-$C_{14}$ fatty acids having a $C_2$-$C_6$ monoamine or diamine moiety. Preferred are monoethanolamides and diethanolamides, particularly fatty monoalkanolamides and fatty dialkanolamides. As disclosed in the examples, linear monoethanolamides are found to be particularly effective and are preferred. These materials may be included in any effective amount. Desirably wherein the treatment block is to be used in an ITB application these one or more mono- or di-alkanol amides are preferably present from 10-30% wt. of the solid block compositions, as well as in the treatment blocks formed therefrom.

The inventive compositions necessarily comprise 5-30% wt., preferably 15-25% wt. of a diluent material. Diluent materials are included to provide additional bulk of the product solid block composition and may enhance leaching out of the surfactant constituent when the solid block composition is placed in water. Exemplary diluent materials include any soluble inorganic alkali, alkaline earth metal salt or hydrate thereof, for example, chlorides such as sodium chloride, magnesium chloride and the like, carbonates and bicarbonates such as sodium carbonate, sodium bicarbonate and the like, sulfates such as magnesium sulfate, copper sulfate, sodium sulfate, zinc sulfate and the like, borax, borates such as sodium borate and the like, as well as others known to the art but not particularly recited herein. Exemplary organic diluents include, inter alia, urea, as well as water soluble high molecular weight polyethylene glycol and polypropylene glycol. Preferred diluent materials and weight percentages thereof are disclosed in the examples.

The inventive compositions necessarily include 0.1-15% wt., preferably 0.5-5% wt. of a filler material of a filler material. Such fillers are typically particulate solid water-insoluble materials which may be based on inorganic materials such as talc or silica, particulate organic polymeric materials such as finely comminuted water insoluble synthetic polymers. Particularly preferred filler materials are disclosed in the examples; silica is particularly preferred for use as a filler material.

The inventive compositions further necessarily comprise 0.05-7% wt., preferably 1-3.5% wt of a bleach constituent. The bleach constituent is relatively inert in the dry state but, which on contact with water, releases oxygen, hypohalite or a halogen especially chlorine. Representative examples of typical oxygen-release bleaching agents, suitable for incorporation in the solid block composition include the alkali metal perborates, e.g., sodium perborate, and alkali metal monopersulfates, e.g., sodium monopersulfates, potassium monopersulfate, alkali metal monoperphosphates, e.g., disodium monoperphosphate and dipotassium monoperphosphate, as well as other conventional bleaching agents capable of liberating hypohalite., e.g., hypochlorite and/or hypobromite, include heterocyclic N-bromo- and N-chloro-cyanurates such as trichloroisocyanuric and tribromoiscyanuric acid, dibromocyanuric acid, dichlorocyanuric acid, N-monobromo-N-mono-chlorocyanuric acid and N-monobromo-N, N-dichlorocyanuric acid, as well as the salts thereof with water solubilizing cations such as potassium and sodium, e.g., sodium N-monobromo-N-monochlorocyanurate, potassium dichlorocyanurate, sodium dichlorocyanurate, as well as other N-bromo and N-chloro-imides, such as N-brominated and N-chlorinated succinimide, malonimide, phthalimide and naphthalimide. Also useful in the solid block composition as hypohalite-releasing bleaches are halohydantoins which may be used include those which may be represented by the general structure:

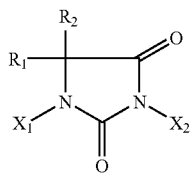

wherein:

$X_1$ and $X_2$ are independently hydrogen, chlorine or bromine; and, $R_1$ and $R_2$ are independently alkyl groups having from 1 to 6 carbon atoms. Examples of halohydantoins include, for example, N,N'-dichloro-dimethyl-hydantoin, N-bromo-N-chloro-dimethyl-hydantoin, N,N'-dibromo-dimethyl-hydantoin, 1,4-dichloro, 5,5-dialkyl substituted hydantoin, wherein each alkyl group independently has 1 to 6 carbon atoms, N-monohalogenated hydantoins such as chlorodimethylhydantoin (MCDMH) and N-bromo-dimethylhydantoin (MBDMH); dihalogenated hydantoins such as dichlorodimethyl-hydantoin (DCDMH), dibromodimethylhydantoin (DBDMH), and 1-bromo-3-chloro-5,5,-dimethylhydantoin (BCDMH); and halogenated methylethylhydantoins such as chloromethylethylhydantion (MCMEH), dichloromethylethylhydantoin (DCMEH), bromomethylethylhydantoin (MBMEH), dibromomethylethylhydantoin (DBMEH), and bromochloromethylethylhydantoin (BCMEH), and mixtures thereof. Other suitable organic hypohalite liberating bleaching agents include halogenated melamines such as tribromomelamine and trichloromelamine. Suitable inorganic hypohalite-releasing bleaching agents include lithium and calcium hypochlorites and hypobromites. The various chlorine, bromine or hypohalite liberating agents may, if desired, be provided in the form of stable, solid complexes or hydrates, such as sodium p-toluene sulfobromamine trihydrate; sodium benzene sulfochloramine dihydrate; calcium hypobromite tetrahydrate; and calcium hypochlorite tetrahydrate. Brominated and chlorinated trisodium phosphates formed by the reaction of the corresponding sodium hypohalite solution with trisodium orthophosphate (and water, as necessary) likewise comprise useful inorganic bleaching agents for incorporation into the inventive solid block composition and the treatment blocks formed therefrom.

Preferably, the bleach constituent necessarily present according to the second aspect of the solid block composition of the invention is a hypohalite liberating compound and more preferably is a hypohalite liberating compound in the form of a solid complex or hydrate thereof. Particularly preferred for use as the bleach constituent are chloroisocynanuric acids and alkali metal salts thereof, preferably potassium, and especially sodium salts thereof. Examples of such compounds include trichloroisocyananuric acid, dichloroisocyanuric acid, sodium dichloroisocyanurate, potassium dichloroisocyanurate, and trichloro-potassium dichloroisocynanurate complex. The most preferred chlorine bleach material is sodium dichloroisocyanurate; the dihydrate of this material is particularly preferred.

The inventive compositions optionally but preferably include a hydrocarbon solvent constituent. The hydrocarbon solvents are immiscible in water, may be linear or branched, saturated or unsaturated hydrocarbons having from about 6 to about 24 carbon atoms, preferably comprising from about 12 to about 16 carbon atoms. Saturated hydrocarbons are preferred, as are branched hydrocarbons. Such hydrocarbon solvents are typically available as technical grade mixtures of two or more specific solvent compounds, and are often petroleum distillates. Nonlimiting examples of some suitable linear hydrocarbons include decane, dodecane, decene, tridecene, and combinations thereof. Mineral oil is one particularly preferred form of a useful hydrocarbon solvent. Paraffin oils are a further particularly preferred form of a useful hydrocarbon surfactant; such include paraffinic hydrocarbons including both linear and branched paraffinic hydrocarbons. The former are commercially available as NORPAR solvents (ex. ExxonMobil Corp.) while the latter are available as ISOPAR solvents (ex. ExxonMobil Corp.) Mixtures of branched hydrocarbons especially as isoparaffins form a further particularly preferred form of a useful hydrocarbon solvent of the invention. Particularly useful technical grade mixtures of isoparaffins include mixtures of isoparaffinic organic solvents having a relatively narrow boiling range. Examples of these commercially available isoparaffinic organic solvents include ISOPAR C described to be primarily a mixture of $C_7$-$C_8$ isoparaffins, ISOPAR E described to be primarily a mixture of $C_8$-$C_9$ isoparaffins, ISOPAR G described to be primarily a mixture of $C_{10}$-$C_{11}$ isoparaffins, ISOPAR H described to be primarily a mixture of $C_{11}$-$C_{12}$ isoparaffins, ISOPAR J, ISOPAR K described to be primarily a mixture of $C_{11}$-$C_{12}$ isoparaffins, ISOPAR L described to be primarily a mixture of $C_{11}$-$C_{13}$ isoparaffins, ISOPAR M described to be primarily a mixture of $C_{13}$-$C_{14}$ isoparaffins, ISOPAR P and ISOPAR V described to be primarily a mixture of $C_{12}$-$C_{20}$ isoparaffins.

Preferred hydrocarbon solvents are those which exhibit a flashpoint of at least about 75° C., preferably at least about 80° C. The flashpoints of the hydrocarbon solvents may be determined according to routine analytical methods, but are frequently recited in the product literature or product specifications available from the supplier of the hydrocarbon solvent.

The hydrocarbon solvent constituent may be present in any effective amount and preferably comprises at least about 0.1% wt. of the total weight of the solid block composition, and the resultant treatment block formed therefrom. Preferably the hydrocarbon solvent constituent is necessarily present and comprises about 1-10% wt., more preferably from about 2-8% wt., and more preferably comprises from about 2.5-6% wt. of the solid block compositions.

According to preferred embodiments of the invention, further organic solvents other than those recited above with reference to the hydrocarbon solvent constituent are absent from the solid block compositions and the treatment blocks taught herein. Such include e.g., alcohols, glycols, and glycol ethers.

The present inventor has surprisingly found that the inclusion of the hydrocarbon solvent constituent in the solid block composition provides several advantageous technical benefits. The inclusion of effective amounts of the hydrocarbon solvent functions as an excellent processing aid during mixing, which decreases the temperature of the solid block composition in mixing and extrusion apparatus used to form the solid mass formed therefrom namely the treatment blocks of the invention. The ability to process at lower temperature also provides for the decreased likelihood of the degradation of one or more of the constituents in the solid block compositions during processing, particularly non-halogen releasing constituents which may be deleteriously affected when contacted with the bleach constituent. Further the inclusion of the hydrocarbon solvent constituent functions as an excellent binding agent which aids in the retention of physical integrity of the treatment block during use either as in an ITB mode or in an ITC mode. Block integrity is advantageously retained in spite of the presence of reactive bleach constituents, which may be present in treatment blocks according to certain aspects of the invention.

In preferred embodiments of the present invention, a hydrocarbon solvent constituent is necessarily present in the inventive compositions, particularly in one of the preferred weight ranges.

The solid treatment blocks may optionally include a film forming constituent in an effective amount. It is to be understood that while the film forming constituent need be present it is not required that the film which is formed on the surface of a lavatory appliance, e.g., toilet bowl, be necessarily uniform either in thickness or in surface coverage although such would be preferred. Rather it is contemplated that film forming materials useful in the present invention need not form a continuous or uniform coating, as it is only required that the film forming materials provide some extent of surface coating to a hard surface upon which it is applied.

A preferred class of materials which find use in the film forming constituent are film forming cationic polymers, an especially film-forming fatty quaternary ammonium compounds which generally conform to the following structure:

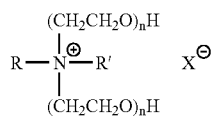

wherein R is a fatty alkyl chain, e.g., $C_8$-$C_{32}$ alkyl chain such as tallow, coco, stearyl, etc., R' is a lower $C_1$-$C_6$ alkyl or alkylene group, the sum of both n is between 12-48, and X is a salt-forming counterion which renders the compound water soluble or water dispersible, e.g., an alkali, alkaline earth metal, ammonium, methosulfate as well as $C_1$-$C_4$ alkyl sulfates.

A particularly preferred film forming film-forming fatty quaternary ammonium compound may be represented by the following structure:

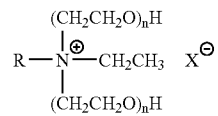

wherein R is a fatty alkyl chain, e.g., $C_8$-$C_{32}$ alkyl chain such as tallow, coco, stearyl, etc., the sum of both "n" is between 12-48, and preferably the value of each n is the same as the other, and X is a salt-forming counterion such as an alkali, alkaline earth metal, ammonium, methosulfate but is preferably an alkyl sulfate such as ethyl sulfate but especially diethyl sulfate. An preferred example of a commercially available material which may be advantageously used is CRODAQUAT TES (ex. Croda Inc., Parsippany, N.J.) described to be polyoxyethylene (16) tallow ethylammonium ethosulfate.

While the film-forming, fatty quaternary ammonium compounds may be present in any effective amount, desirably it is present in amounts of from 0.01-20% wt., more desirably from 0.01-15% wt. based on the total weight of the inventive compositions.

Further exemplary film forming materials are film-forming, organosilicone quaternary ammonium compounds. Such compounds may also exhibit antimicrobial activity, especially on hard surfaces which may supplement the effect of the quaternary ammonium surfactant compounds having germicidal properties.

Specific examples of organosilicone quaternary ammonium salts that may be used in the compositions of this invention include organosilicone derivatives of the following ammonium salts: di-isobutylcresoxyethoxyethyl dimethyl benzyl ammonium chloride, di-isobutylphenoxyethoxyethyl dimethyl benzyl ammonium chloride, myristyl dimethylbenzyl ammonium chloride, myristyl picolinium chloride, N-ethyl morpholinium chloride, laurylisoquinolinium bromide, alkyl imidazolinium chloride, benzalkonium chloride, cetyl pyridinium chloride, coconut dimethyl benzyl ammonium chloride, stearyl dimethyl benzyl ammonium chloride, alkyl dimethyl benzyl ammonium chloride, alkyl diethyl benzyl ammonium chloride, alkyl dimethyl benzyl ammonium bromide, di-isobutyl phenoxyethoxyethyl trimethyl ammonium chloride, di-isobutylphenoxyethoxyethyl dimethyl alkyl ammonium chloride, methyl-dodecylbenzyl trimethyl ammonium chloride, cetyl trimethyl ammonium bromide, octadecyl dimethyl ethyl ammonium bromide, cetyl dimethyl ethyl ammonium bromide, octadec-9-enyl dimethyl ethyl ammonium bromide, dioctyl dimethyl ammonium chloride, dodecyl trimethyl ammonium chloride, octadecyl trimethyl ammonium chloride, octadecyl trimethyl ammonium bromide, hexadecyl trimethyl ammonium iodide, octyl trimethyl ammonium fluoride, and mixtures thereof. Other water dispersible salts, such as the acetates, sulfates, nitrates, and phosphates, are effective in place of the halides, but the chlorides and bromides are preferred. The silicone group is preferably substituted with alkyl ethers. Preferred alkyl ethers are short carbon chain ethers such as methoxy and ethoxy substituents.

Examples of particularly preferred film-forming, organosilicone quaternary ammonium compounds which find use in the present inventive compositions include those which may be represented by the following structural representation:

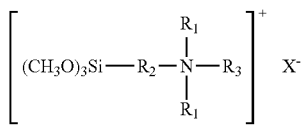

wherein:
$R_1$ and $R_2$ each independently represent short chain alkyl or alkenyl groups, preferably $C_1$-$C_8$ alkyl or alkenyl groups;
$R_3$ represents a $C_{11}$-$C_{22}$ alkyl group; and
X represents a salt forming counterion, especially a halogen.

Preferred short chain alkyl substituents for $R_1$ are methyl and ethyl, preferred short chain alkyl substituents for $R_2$ are straight chain links of methylene groups consisting of from 1 to 4 members, preferred $R_3$ substituents are straight chain links of methylene groups consisting of from 11 to 22 members, and preferred halogens for X are chloride and bromide.

A particularly preferred and commercially available film-forming, organosilicone quaternary ammonium compounds useful in the inventive compositions is AEM® 5772 or AEM® 5700 (from Aegis Environmental Co., Midland, Mich.). Both of these materials are described as being 3-(trimethoxysilyl)propyloctadecyldimethyl ammonium chloride, AEM® 5700 and is sold as a 42% by weight active solution of the compound in a water/methanol mixture, while AEM® 5772 is sold as a 72% by weight active solution of the compound in a water/methanol mixture. While the film-forming, organosilicone quaternary ammonium compound may be present in any effective amount, desirably it is present in amounts of from 0.05-20% wt., more desirably from 0.05-15% wt. based on the total weight of the inventive compositions.

It is of course contemplated that a mixture or blend of two or more distinct compounds may be used to provide the film forming constituent of the inventive compositions.

In addition to the film forming materials described immediately above, other film forming materials which are compatible with the balance of the constituents present in an inventive composition are also contemplated as being useful and within the scope of the present invention.

In preferred embodiments of the present invention, a film forming polymer constituent is necessarily present in the inventive compositions, particularly in one of the preferred weight ranges.

In addition to the foregoing essential constituents, the inventive compositions may include, up to 50% wt. or one or more further additive constituents, including but not limited to: binders, fragrances, processing aids such as lubricants and tabletting aids, bleaches, sanitizing compositions and the like. These optional constituents may be incorporated into the blocks of the invention as long as they do not adversely affect the properties of the treatment block formed from the solid block composition In addition to the essential linear alkyl benzene sulfonate and alkyl olefin sulfonates, the inventive compositions may include one or more cosurfactants in detersive effective amounts. Exemplary useful cosurfactants include further anionic, nonionic, cationic, amphoteric, and zwitterionic surfactants, particularly those whose melting points are sufficiently high, above about 110° F., preferably above 125° F., to permit processing according to known art techniques. However, small amounts of low melting point surfactants and even liquid surfactants may be used in providing the surfactant constituent.

Exemplary useful anionic surfactants which may be used as cosurfactants in the solid block composition of the invention can be broadly described as the water-soluble salts, particularly the alkali metal salts, of organic sulfuric acid reaction products having in their molecular structure an alkyl or alkaryl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic surfactants which can be employed in practicing the present invention are the sodium or potassium alkyl sulfates, especially those obtained by sulfating the higher alcohols ($C_8$-$C_{18}$ carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); alkyl olefin sulfonate surfactants having the general formula $RSO_3$ M, wherein R is a primary or secondary alkyl group containing from about 8 to about 24 carbon atoms (preferably 10 to 18 carbon atoms) and M is an alkali metal, e.g., sodium, lithium or potassium; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 10 moles of ethylene oxide; sodium or potassium salts of alkyl phenol ethylene oxide ether sulfates with about 1 to about 10 units of ethylene oxide per molecule and in which the alkyl radicals contain from about 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium β-acetoxy- or β-acetamido-alkanesulfonates where the alkane has from 8 to 22 carbon atoms.

One or more nonionic surfactants may be present as cosurfactants in the inventive compositions. Practically any hydrophobic compound having a carboxy, hydroxy, amido, or amino group with a free hydrogen attached to the nitrogen can be condensed with an alkylene oxide, especially ethylene oxide or with the polyhydration product thereof, a polyalkylene glycol, especially polyethylene glycol, to form a water soluble or water dispersible nonionic surfactant compound. Further, the length of the polyethenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

One class of useful nonionic surfactants include polyalkylene oxide condensates of alkyl phenols. These compounds include the condensation products of alkyl phenols having an alkyl group containing from about 6 to 12 carbon atoms in either a straight chain or branched chain configuration with an alkylene oxide, especially an ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

A further class of useful nonionic surfactants include the condensation products of aliphatic alcohols with from about 1 to about 60 moles of an alkylene oxide, especially an ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol and the condensation product of about 9 moles of ethylene oxide with coconut alcohol (a mixture of fatty alcohols with alkyl chains varying in length from about 10 to 14 carbon atoms). Other examples are those $C_6$-$C_{11}$ straight-chain alcohols which are ethoxylated with from about 3 to about 6 moles of ethylene oxide. Their derivation is well known in the art. Examples include Alfonic® 810-4.5, which is described in product literature from Sasol as a $C_8$-$C_{10}$ straight-chain alcohol having an average molecular weight of 356, an ethylene oxide content of about 4.85 moles (about 60 wt. %), and an HLB of about 12; Alfonic® 810-2, which is described in product literature as a $C_8$-$C_{10}$ straight-chain alcohols having an average molecular weight of 242, an ethylene oxide content of about 2.1 moles (about 40 wt. %), and an HLB of about 12; and Alfonic® 610-3.5, which is described in product literature as having an average molecular weight of 276, an ethylene oxide content of about 3.1 moles (about 50 wt. %), and an HLB of 10. Other examples of alcohol ethoxylates are $C_{10}$ oxo-alcohol ethoxylates available from BASF under the Lutensol® ON tradename. They are available in grades containing from about 3 to about 11 moles of ethylene oxide (available under the names Lutensol® ON 30; Lutensol® ON 50; Lutensol® ON 60; Lutensol® ON 65; Lutensol® ON 66; Lutensol® ON 70; Lutensol® ON 80; and Lutensol® ON 110). Other examples of ethoxylated alcohols include the Neodol® 91 series non-ionic surfactants available from Shell Chemical Company which are described as $C_9$-$C_{11}$ ethoxylated alcohols. The Neodol® 91 series non-ionic surfactants of interest include Neodol® 91-2.5, Neodol® 91-6, and Neodol® 91-8. Neodol® 91-2.5 has been described as having about 2.5 ethoxy groups per molecule; Neodol 91-6 has been described as having about 6 ethoxy groups per molecule; and Neodol 91-8 has been described as having about 8 ethoxy groups per molecule. Further examples of ethoxylated alcohols include the Rhodasurf® DA series non-ionic surfactants available from Rhodia which are described to be branched isodecyl alcohol ethoxylates. Rhodasurf® DA-530 has been described as having 4 moles of ethoxylation and an HLB of 10.5; Rhodasurf® DA-630 has been described as having 6 moles of ethoxylation with an HLB of 12.5; and Rhodasurf® DA-639 is a 90% solution of DA-630. Further examples of ethoxylated alcohols include those from Tomah Products (Milton, Wis.) under the Tomadol® tradename with the formula $RO(CH_2CH_2O)_nH$ where R is the primary linear alcohol and n is the total number of moles of ethylene oxide. The ethoxylated alcohol series from Tomah include 91-2.5; 91-6; 91-8— where R is linear $C_9$/$C_{10}$/$C_{11}$ and n is 2.5, 6, or 8; 1-3; 1-5; 1-7; 1-73B; 1-9; where R is linear $C_{11}$ and n is 3, 5, 7 or 9; 23-1; 23-3; 23-5; 23-6.5—where R is linear $C_{12}$/$C_{13}$ and n is 1, 3, 5, or 6.5; 25-3; 25-7; 25-9; 25-12—where R is linear $C_{12}$/$C_{13}$/$C_{14}$/$C_{15}$ and n is 3, 7, 9, or 12; and 45-7; 45-13—where R is linear $C_{14}$/$C_{15}$ and n is 7 or 13.

A further class of useful nonionic surfactants include primary and secondary linear and branched alcohol ethoxylates, such as those based on $C_6$-$C_{18}$ alcohols which further include an average of from 2 to 80 moles of ethoxylation per mol of alcohol. These examples include the Genapol® UD (ex. Clariant, Muttenz, Switzerland) described under the tradenames Genapol® UD 030, $C_{11}$-oxo-alcohol polyglycol ether with 3 EO; Genapol® UD, 050 $C_{11}$-oxo-alcohol polyglycol ether with 5 EO; Genapol® UD 070, $C_{11}$-oxo-alcohol polyglycol ether with 7 EO; Genapol® UD 080, $C_{11}$-oxo-alcohol polyglycol ether with 8 EO; Genapol® UD 088, $C_{11}$-oxo-alcohol polyglycol ether with 8 EO; and Genapol® UD 110, $C_{11}$-oxo-alcohol polyglycol ether with 11 EO.

Exemplary useful nonionic surfactants include the condensation products of a secondary aliphatic alcohols containing 8 to 18 carbon atoms in a straight or branched chain configuration condensed with 5 to 30 moles of ethylene oxide. Examples of commercially available nonionic detergents of the foregoing type are those presently commercially available under the trade name of Tergitol® such as Tergitol 15-S-12 which is described as being $C_{11}$-$C_{15}$ secondary alkanol condensed with 9 ethylene oxide units, or Tergitol 15-S-9 which is described as being $C_{11}$-$C_{15}$ secondary alkanol condensed with 12 ethylene oxide units per molecule.

A further class of useful nonionic surfactants include those surfactants having a formula:

$$RO(CH_2CH_2O)_nH$$

wherein;

R is a mixture of linear, even carbon-number hydrocarbon chains ranging from $C_{12}H_{25}$ to $C_{16}H_{33}$ and n represents the number of ethoxy repeating units and is a number of from about 1 to about 12.

Surfactants of this formula are presently marketed under the Genapol® tradename (ex. Clariant), which surfactants include the "26-L" series of the general formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from 1 to about 12, such as 26-L-1, 26-L-1.6, 26-L-2, 26-L-3, 26-L-5, 26-L-45, 26-L-50, 26-L-60, 26-L-60N, 26-L-75, 26-L-80, 26-L-98N, and the 24-L series, derived from synthetic sources and typically contain about 55% $C_{12}$ and 45% $C_{14}$ alcohols, such as 24-L-3, 24-L-45, 24-L-50, 24-L-60, 24-L-60N, 24-L-75, 24-L-92, and 24-L-98N, all sold under the Genapol® tradename.

Further useful non-ionic surfactants which may be used in the inventive compositions include those presently marketed under the trade name Pluronics® (ex. BASF). The compounds are formed by condensing ethylene oxide with a hydrophobic base formed by the condensation of propylene oxide with propylene glycol. The molecular weight of the hydrophobic portion of the molecule is of the order of 950 to 4,000 and preferably 200 to 2,500. The addition of polyoxyethylene radicals of the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants are in liquid form and particularly satisfactory surfactants are available as those marketed as Pluronics® L62 and Pluronics® L64.

Further nonionic surfactants which may be included in the inventive compositions include alkoxylated alkanolamides, preferably $C_8$-$C_{24}$ alkyl di($C_2$-$C_3$ alkanol amides), as represented by the following formula:

$$R_5\text{—}CO\text{—}NH\text{—}R_6\text{—}OH$$

wherein $R_5$ is a branched or straight chain $C_8$-$C_{24}$ alkyl radical, preferably a $C_{10}$-$C_{16}$ alkyl radical and more preferably a $C_{12}$-$C_{14}$ alkyl radical, and 6 is a $C_1$-$C_4$ alkyl radical, preferably an ethyl radical.

According to certain particularly preferred embodiments the detersive surfactant constituent necessarily comprises a nonionic surfactant based on a linear primary alcohol ethoxylate particularly wherein the alkyl portion is a $C_8$ to $C_{16}$, but particularly a $C_9$ to $C_{11}$ alkyl group, and having an average of between about 6 to about 8 moles of ethoxylation.

One further useful class of nonionic surfactants include those in which the major portion of the molecule is made up of block polymeric $C_2$-$C_4$ alkylene oxides, with alkylene oxide blocks containing $C_3$ to $C_4$ alkylene oxides. Such nonionic surfactants, while preferably built up from an alkylene oxide chain starting group, can have as a starting nucleus almost any active hydrogen containing group including, without limitation, amides, phenols, and secondary alcohols.

One group of nonionic surfactants containing the characteristic alkylene oxide blocks are those which may be generally represented by the formula (A):

$$\text{HO-}(EO)_x(PO)_y EO)_z\text{—H} \quad (A)$$

where EO represents ethylene oxide,
PO represents propylene oxide,
y equals at least 15,
$(EO)_{x+z}$ equals 20 to 50% of the total weight of said compounds, and,
the total molecular weight is preferably in the range of about 2000 to 15,000.

Another group of nonionic surfactants appropriate for use in the new compositions can be represented by the formula (B):

$$R\text{-}(EO,PO)_a(EO,PO)_b\text{—H} \quad (B)$$

wherein R is an alkyl, aryl or aralkyl group,
the alkoxy group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by Formula B include butoxy derivatives of propylene oxide/ethylene oxide block polymers having molecular weights within the range of about 2000-5000.

Still further useful nonionic surfactants containing polymeric butoxy (BO) groups can be represented by formula (C) as follows:

$$RO\text{—}(BO)_n(EO)_x\text{—H} \quad (C)$$

wherein R is an alkyl group containing 1 to 20 carbon atoms,
n is about 15 and x is about 15.

Also useful as the nonionic block copolymer surfactants which also include polymeric butoxy groups are those which may be represented by the following formula (D):

$$\text{HO-}(EO)_x(BO)_n(EO)_y\text{—H} \quad (D)$$

wherein n is about 15,
x is about 15 and
y is about 15.

Still further useful nonionic block copolymer surfactants include ethoxylated derivatives of propoxylated ethylene diamine, which may be represented by the following formula:

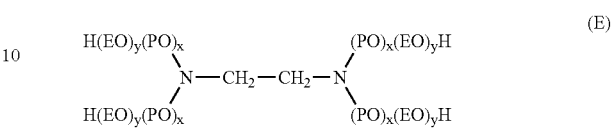
(E)

where (EO) represents ethoxy,
(PO) represents propoxy,
the amount of $(PO)_x$ is such as to provide a molecular weight prior to ethoxylation of about 300 to 7500, and the amount of $(EO)_y$ is such as to provide about 20% to 90% of the total weight of said compound.

Further useful nonionic surfactants include nonionic amine oxide constituent. Exemplary amine oxides include:

i) Alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide;

ii) Alkyl di (hydroxy lower alkyl) amine oxides in which the alkyl group has about 10-20, and preferably 12-16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide;

iii) Alkylamidopropyl di(lower alkyl) amine oxides in which the alkyl group has about 10-20, and preferably 12-16 carbon atoms, and can be straight or branched chain, saturated or unsaturated. Examples are cocoamidopropyl dimethyl amine oxide and tallowamidopropyl dimethyl amine oxide; and iiii) Alkylmorpholine oxides in which the alkyl group has about 10-20, and preferably 12-16 carbon atoms, and can be straight or branched chain, saturated or unsaturated.

Preferably the amine oxide constituent is an alkyl di (lower alkyl) amine oxide as denoted above and which may be represented by the following structure:

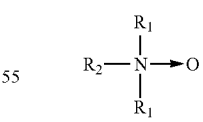

wherein each:
$R_1$ is a straight chained $C_1$-$C_4$ alkyl group, preferably both $R_1$ are methyl groups; and,
$R_2$ is a straight chained $C_8$-$C_{18}$ alkyl group, preferably is $C_{10}$-$C_{14}$ alkyl group, most preferably is a $C_{12}$ alkyl group.

Each of the alkyl groups may be linear or branched, but most preferably are linear. Most preferably the amine oxide constituent is lauryl dimethyl amine oxide. Technical grade mixtures of two or more amine oxides may be used, wherein, amine oxides of varying chains of the $R_2$ group are present. Preferably, the amine oxides used in the present invention include $R_2$ groups which comprise at least 50% wt., preferably at least 60% wt. of $C_{12}$ alkyl groups and at least 25% wt. of $C_{14}$ alkyl groups, with not more than 15% wt. of $C_{16}$, $C_{18}$ or higher alkyl groups as the $R_2$ group.

Still further exemplary useful nonionic surfactants which may be used include certain alkanolamides including monoethanolamides and diethanolamides, particularly fatty monoalkanolamides and fatty dialkanolamides.

A cationic surfactant may be incorporated as a germicide or as a detersive surfactant in the solid block composition of the present invention, particularly wherein a bleach constituent is absent from the solid block composition. Cationic surfactants are per se, well known, and exemplary useful cationic surfactants may be one or more of those described for example in *McCutcheon's Functional Materials, Vol. 2*, 1998; *Kirk-Othmer, Encyclopedia of Chemical Technology*, 4th Ed., Vol. 23, pp. 481-541 (1997), the contents of which are herein incorporated by reference. These are also described in the respective product specifications and literature available from the suppliers of these cationic surfactants.

Examples of preferred cationic surfactant compositions useful in the practice of the instant invention are those which provide a germicidal effect to the concentrate compositions, and especially preferred are quaternary ammonium compounds and salts thereof, which may be characterized by the general structural formula:

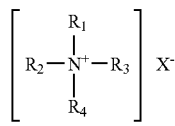

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxy-alkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

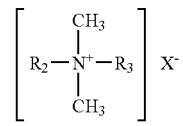

wherein $R_2$ and $R_3$ are the same or different $C_8$-$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Such useful quaternary compounds are available under the BARDAC®, BARQUAT®, HYAMINE®, LONZABAC®, and ONYXIDE® trademarks, which are more fully described in, for example, *McCutcheon's Functional Materials* (Vol. 2), North American Edition, 1998, as well as the respective product literature from the suppliers identified below. For example, BARDAC® 205M is described to be a liquid containing alkyl dimethyl benzyl ammonium chloride, octyl decyl dimethyl ammonium chloride; didecyl dimethyl ammonium chloride, and dioctyl dimethyl ammonium chloride (50% active) (also available as 80% active (BARDAC® 208M)); described generally in *McCutcheon's* as a combination of alkyl dimethyl benzyl ammonium chloride and dialkyl dimethyl ammonium chloride); BARDAC® 2050 is described to be a combination of octyl decyl dimethyl ammonium chloride/didecyl dimethyl ammonium chloride, and dioctyl dimethyl ammonium chloride (50% active) (also available as 80% active (BARDAC® 2080)); BARDAC® 2250 is described to be didecyl dimethyl ammonium chloride (50% active); BARDAC® LF (or BARDAC® LF-80), described as being based on dioctyl dimethyl ammonium chloride (BARQUAT® MB-50, MX-50, OJ-50 (each 50% liquid) and MB-80 or MX-80 (each 80% liquid) are each described as an alkyl dimethyl benzyl ammonium chloride; BARDAC® 4250 and BARQUAT® 4250Z (each 50% active) or BARQUAT® 4280 and BARQUAT 4280Z (each 80% active) are each described as alkyl dimethyl benzyl ammonium chloride/alkyl dimethyl ethyl benzyl ammonium chloride. Also, HYAMINE® 1622, described as diisobutyl phenoxy ethoxy ethyl dimethyl benzyl ammonium chloride (50% solution); HYAMINE® 3500 (50% actives), described as alkyl dimethyl benzyl ammonium chloride (also available as 80% active (HYAMINE® 3500-80)); and HYAMINE® 2389 described as being based on methyldodecylbenzyl ammonium chloride and/or methyldodecylxylene-bis-trimethyl ammonium chloride. (BARDAC®, BARQUAT® and HYAMINE® are presently commercially available from Lonza, Inc., Fairlawn, N.J.). BTC® 50 NF (or BTC® 65 NF) is described to be alkyl dimethyl benzyl ammonium chloride (50% active); BTC® 99 is described as didecyl dimethyl ammonium chloride (50% active); BTC® 776 is described to be myrisalkonium chloride (50% active); BTC® 818 is described as being octyl decyl dimethyl ammonium chloride, didecyl dimethyl ammonium chloride, and dioctyl dimethyl ammonium chloride (50% active) (available also as 80% active (BTC® 818-80%)); BTC® 824 and BTC® 835 are each described as being of alkyl dimethyl benzyl ammonium chloride (each 50% active); BTC® 885 is described as a combination of BTC® 835 and BTC® 818 (50% active) (available also as 80% active (BTC® 888)); BTC® 1010 is described as didecyl dimethyl ammonium chloride (50% active) (also available as 80% active (BTC® 1010-80)); BTC® 2125 (or BTC® 2125 M) is described as alkyl dimethyl benzyl ammonium chloride and alkyl dimethyl ethylbenzyl ammonium chloride (each 50% active) (also available as 80% active (BTC® 2125 80 or BTC® 2125 M); BTC® 2565 is described as alkyl dimethyl benzyl ammonium chlorides (50% active) (also available as 80% active (BTC® 2568)); BTC® 8248 (or BTC® 8358) is described as alkyl dimethyl benzyl ammonium chloride (80% active) (also available as 90% active (BTC® 8249)); ONYXIDE® 3300 is described as n-alkyl dimethyl benzyl ammonium saccharinate (95% active). (BTC® and ONYXIDE® are presently commercially available from Stepan Company, Northfield, Ill.) Polymeric quaternary ammonium salts based on these monomeric structures are also considered desirable for the present invention. One example is POLYQUAT®, described as being a 2-butenyldimethyl ammonium chloride polymer.

When present in a solid block composition, it is preferred that the germicidal cationic surfactant(s) are present in amounts so to dispense at least about 200 parts per million (ppm) in the water flushed into the sanitary appliance, e.g., toilet bowl, or into the water retained in the sanitary appliance at the conclusion of the flush cycle.

Further detersive surfactants which may be included are amphoteric and zwitterionic surfactants which provide a detersive effect. Exemplary useful amphoteric surfactants include alkylbetaines, particularly those which may be represented by the following structural formula:

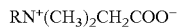
$RN^+(CH_3)_2CH_2COO^-$ wherein R is a straight or branched hydrocarbon chain which may include an aryl moiety, but is preferably a straight hydrocarbon chain containing from about 6 to 30 carbon atoms. Further exemplary useful amphoteric surfactants include amidoalkylbetaines, such as amidopropylbetaines which may be represented by the following structural formula:

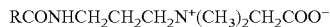
$RCONHCH_2CH_2CH_2N^+(CH_3)_2CH_2COO^-$ wherein R is a straight or branched hydrocarbon chain which may include an aryl moiety, but is preferably a straight hydrocarbon chain containing from about 6 to 30 carbon atoms.

As noted above, preferred detersive surfactants are those which exhibit a melting points above about 110° F., preferably above 125° F., in order to permit convenient processing according to known art techniques. Nonetheless small amounts of low melting point surfactants, i.e., those exhibiting melting points below about 110° F. and even liquid surfactants may be used in providing the surfactant constituent of the solid block composition.

As the performance requirements of treatment blocks may differ according to their use as either an ITB or as an ITC block, the amounts of the constituents present in the block may vary as well depending upon the final intended use of the treatment block.

When intended for use as an ITB block, the cosurfactant constituent may be present in any effective amount and may comprise up to about 50% wt. of the total weight of the solid block composition, and the resultant treatment block formed therefrom.

Notwithstanding the potential use of one or more cosurfactants, as noted previously, according to certain particularly preferred embodiments no cosurfactants are present in the inventive compositions.

As the performance requirements of treatment blocks may differ according to their use as either an ITB or as an ITC block, the amounts of the constituents present in the block may vary as well depending upon the final intended use of the treatment block.

The inventive solid block compositions may optionally include one or more colorants used to impart a color to the solid block composition, or to the water with which the solid block composition contacts or both. Exemplary useful colorants include any materials which may provide a desired coloring effect. Exemplary useful coloring agents include dyes, e.g., Alizarine Light Blue B (C.I. 63010), Carta Blue VP (C.I. 24401), Acid Green 2G (C.I. 42085), Astragon Green D (C.I. 42040) Supranol Cyanine 7B (C.I. 42675), Maxilon Blue 3RL (C.I. Basic Blue 80), acid yellow 23, acid violet 17, a direct violet dye (Direct violet 51), Drimarine Blue Z-RL (C.I. Reactive Blue 18), Alizarine Light Blue H-RL (C.I. Acid Blue 182), FD&C Blue No. 1, FD&C Green No. 3 and Acid Blue No. 9. When a bleach constituent is included in the solid block composition, the colorant, e.g., dye, should be selected so to ensure the compatibility of the colorant with the bleach constituent, or so that its color persists despite the presence in the toilet bowl of a concentration of hypochlorite which is effective to maintain sanitary conditions. Frequently however, a solid block composition which includes a bleach constituent do not comprise any colorants. Desirably the colorants, when present, do not exceed 15% wt. of the solid block composition, although generally lesser amounts are usually effective.

The solid block composition of the invention may include one or more perfumes or fragrances which impart desirable scent characteristics to the solid blocks formed from the solid block composition taught herein. Exemplary perfumes may be any material giving an acceptable odor and thus materials giving a "disinfectant" odor such as essential oils, pine extracts, terpinolenes, ortho phenyl phenol or paradichlorobenzene may be employed. The essential oils and pine extracts also contribute as plasticizers and are functional to a degree in extending block life. The perfume may be in solid form and is suitably present in an amount up to 10% by weight of the solid block composition.

Further optional constituents are stain inhibiting materials. The solid block composition of the invention may, for example, include an effective amount of a manganese stain inhibiting agent which is advantageously included wherein the sanitary appliance is supplied by a water source having an appreciable or high amount of manganese. Such water containing a high manganese content are known to frequently deposit unsightly stains on surfaces of sanitary appliances, especially when the solid block composition also contains a bleach source which provides a hypochlorite. To counteract such an effect the solid block composition of the present invention may comprise a manganese stain inhibiting agent, such as a partially hydrolyzed polyacrylamide having a molecular weight of about 2000 to about 10,000, a polyacrylate with a molecular weight of about 2000 to about 10,000, and/or copolymers of ethylene and maleic acid anhydride with a molecular weight of from about 20,000 to about 100,000. When present the satin inhibiting materials may comprise to about 110% wt.

The solid block composition of the invention may include a germicide. Exemplary suitable germicides include, for example, formaldehyde release agents, chlorinated phenols, as well as iodophors. It is to be understood that certain cationic surfactants including quaternary ammonium compound based surfactants may also provide a germicidal benefit and may be used in place of the optional further germicide constituent recited here. Further exemplary useful germicides which may be included include methylchloroisothiazolinone/methylisothiazolinone sodium sulfite, sodium bisulfite, imidazolidinyl urea, diazolidinyl urea, benzyl alcohol, 2-bromo-2-nitropropane-1,3-diol, formalin (formaldehyde), iodopropenyl butylcarbamate, chloroacetamide, methanamine, methyldibromonitrile glutaronitrile, glutaraldehyde, 5-bromo-5-nitro-1,3-dioxane, phenethyl alcohol, o-phenylphenol/sodium o-phenylphenol, sodium hydroxymethylglycinate, polymethoxy bicyclic oxazolidine, dimethoxane, thimersal dichlorobenzyl alcohol, captan, chlorphenenesin, dichlorophene, chlorbutanol, glyceryl laurate, halogenated diphenyl ethers, phenolic compounds, mono- and poly-alkyl and aromatic halophenols, resorcinol and its derivatives, bisphenolic compounds, benzoic esters (parabens), halogenated carbanilides, 3-trifluoromethyl-4,4'-dichlorocarbanilide, and 3,3',4-trichlorocarbanilide. More preferably, the non-cationic antimicrobial agent is a mono- and poly-alkyl and aromatic halophenol selected from the group p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m,m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, and 5-chloro-2-hydroxydiphenylmethane.

When present the germicide is included in the solid block composition in germicidally effective amounts.

A further optional constituent are one or more preservatives. Such preservatives are primarily included to reduce the growth of undesired microorganisms within the treatment blocks formed from the solid block composition during storage prior to use or while used, although it is expected that the such a preservative may impart a beneficial antimicrobial effect to the water in the sanitary appliance to which the treatment block is provided. Exemplary useful preservatives include compositions which include parabens, including methyl parabens and ethyl parabens, glutaraldehyde, formaldehyde, 2-bromo-2-nitropropane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. For reasons of availability, the most preferred preservative are those commercially available preservative comprising a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.). Further useful preservative compositions include KATHON® CG/ICP II, a further preservative composition presently commercially available from Rohm and Haas (Philadelphia, Pa.), PROXEL® which is presently commercially available from Zeneca Biocides (Wilmington, Del.), SUTTOCIDE® A which is presently commercially available from Sutton Laboratories (Chatam, N.J.) as well as TEXTAMER® 38AD which is presently commercially available from Calgon Corp. (Pittsburgh, Pa.). When present, the optional preservative constituent should not exceed about 5% wt. of the solid block composition, although generally lesser amounts are usually effective.

The inventive solid block composition may include a binder constituent. The binder may function in part controlling the rate of dissolution of the tablet. The binder constituent may be a clay, but preferably is a water-soluble or water-dispersible gel-forming organic polymer. The term "gel-forming" as applied to this polymer is intended to indicate that on dissolution or dispersion in water it first forms a gel which, upon dilution with further water, is dissolved or dispersed to form a free-flowing liquid. The organic polymer serves essentially as binder for the tablets produced in accordance with the invention although, as will be appreciated, certain of the polymers envisaged for use in accordance with the invention also have surface active properties and thereby serve not only as binders but also enhance the cleansing ability of the tablets of the invention. Further certain organic polymers, such as substituted celluloses, also serve as soil antiredeposition agents. A wide variety of water-soluble organic polymers are suitable for use in the solid block composition of the present invention. Such polymers may be wholly synthetic or may be semi-synthetic organic polymers derived from natural materials. Thus, for example, on class of organic polymers for use in accordance with the invention are chemically modified celluloses such as ethyl cellulose, methyl cellulose, sodium carboxymethyl cellulose, hydroxypropyl cellulose, hydroxypropyl methyl cellulose, ethyl hydroxyethyl cellulose, carboxymethyl hydroxyethyl cellulose, and hydroxyethyl cellulose. Another class of organic polymers which may be used include naturally derived or manufactured (fermented) polymeric materials such as alginates and carageenan. Also, water-soluble starches and gelatin may be used as the optional binder constituent. The cellulose based binders are a preferred class of binders for use in the solid block composition and may possess the property of inverse solubility that is their solubility decreases with increasing temperature, thereby rendering the tablets of the invention suitable for use in locations having a relatively high ambient temperature.

The optional binder constituent may also be one or more synthetic polymers e.g, polyvinyl alcohols; water-soluble partially hydrolyzed polyvinyl acetates; polyacrylonitriles; polyvinyl pyrrolidones; water-soluble polymers of ethylenically unsaturated carboxylic acids, such as acrylic acid and methacrylic acid, and salts thereof; base-hydrolysed starch-polyacrylonitrile copolymers; polyacrylamides; ethylene oxide polymers and copolymers; as well as carboxypolymethylenes.

In the case of the organic polymeric binders it may be noted that, in general, the higher the molecular weight of the polymer the greater the in-use life of the treatment block of the invention. When present, the total binder content may comprise up to 40% wt. of the solid block composition, but preferably is from 0.5 to 40% by weight, preferably from 1 to 65% by weight, more preferably from 5 to 40% by weight.

The solid block composition may optionally include one or more water-softening agents or one or more chelating agents, for example inorganic water-softening agents such as sodium hexametaphosphate or other alkali metal polyphosphates or organic water-softening agents such as ethylenediaminetetraacetic acid and nitrilotriacetic acid and alkali metal salts thereof. When present, such water-softening agents or chelating agents should not exceed about 20% wt. of the solid block composition, although generally lesser amounts are usually effective.

The solid block composition may optionally include one or more solid water-soluble acids or acid-release agents such as sulfamic acid, citric acid or sodium hydrogen sulfate. When present, such solid water-soluble acids or acid-release agents should not exceed about 20% wt. of the solid block composition, although generally lesser amounts are usually effective.

The solid block composition and treatment blocks formed therefrom may include one or more further processing aids. For example, the solid block composition may also include other binding and/or plasticizing ingredients serving to assist in the manufacture thereof, for example, polypropylene glycol having a molecular weight from about 300 to about 10,000 in an amount up to about 20% by weight, preferably about 4% to about 15% by weight of the mixture may be used. The polypropylene glycol reduces the melt viscosity, acts as a demolding agent and also acts to plasticize the block when the composition is prepared by a casting process. Other suitable plasticizers such as pine oil fractions, d-limonene, dipentene and the ethylene oxide-propylene oxide block copolymers may be utilized. Other useful processing aids include tabletting lubricants such as metallic stearates, stearic acid, paraffin oils or waxes or sodium borate which facilitate in the formation of the treatment blocks in a tabletting press or die. Further useful constituents which may also be used include lubricants or other processing aids which facilitate in the manufacture of treatment blocks by extrusion processes. By way of example such materials include, inter alia, stearates, paraffinic hydrocarbons such as the use of materials sold as Isopar® solvents (ex. Exxon Chemical) described previously, as well as diester compounds which are one or more compounds which may be represented by the following structure:

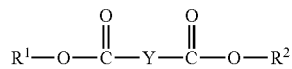

wherein:

$R^1$ and $R^2$ can independently be $C_1$-$C_6$ alkyl which may optionally substituted, Y is $(CH_2)_x$, wherein x is 0-10, but is preferably 1-8, and while Y may be a linear alkyl or phenyl moiety, desirably Y includes one or more oxygen atoms and/or is a branched moiety.

Exemplary diester constituents include the following diester compounds according to the foregoing structure: dimethyl oxalate, diethyl oxalate, diethyl oxalate, dipropyl oxalate, dibutyl oxalate, diisobutyl oxalate, dimethyl succinate, diethyl succinate, diethylhexyl succinate, dimethyl glutarate, diisostearyl glutarate, dimethyl adipate, diethyl adipate, diisopropyl adipate, dipropyl adipate, dibutyl adipate, diisobutyl adipate, dihexyladipate, di-C12-15-alkyl adipate, dicapryl adipate, dicetyl adipate, diisodecyl adipate, diisocetyl adipate, diisononyl adipate, diheptylundecyl adipate, ditridecyl adipate, diisostearyl adipate, diethyl sebacate, diisopropyl sebacate, dibutyl sebacate, diethylhexylsebacate, diisocetyl dodecanedioate, dimethyl brassylate, dimethyl phthalate, diethyl phthalate, dibutyl phthalate. Preferred diester constituents include those wherein Y is $-(CH_2)_x-$ wherein x has a value of from 0-6, preferably a value of 0-5, more preferably a value of from 1-4, while $R^1$ and $R^2$ are $C_1$-$C_6$ alkyl groups which may be straight chained alkyl but preferably are branched, e.g, iso- and tert-moieties. Particularly preferred diester compounds are those in which the compounds terminate in ester groups.

When present such further processing aids are typically included in amounts of up to about 50%, preferably to 25%, more preferably to 20% by weight of the solid block composition, although generally lesser amounts are usually effective.

Ideally the treatment blocks formed from the solid block composition exhibit a density greater than that of water which ensures that they will sink when suspended in a body of water, e.g., the water present within a cistern. Preferably the treatment blocks formed from the solid block composition exhibit a density in excess of about 1 g/cc of water, preferably a density in excess of about 1.5 g/cc of water and most preferably a density of at least about 2 g/cc of water.

The treatment blocks according to the present invention may also be provided with a coating of a water-soluble film, such as polyvinyl acetate following the formation of the treatment blocks from the recited solid block composition. Such may be desired for improved handling, however such is often unnecessary as preferred embodiments of the treatment blocks exhibit a lower likelihood of sticking to one another following manufacture than many prior art treatment block compositions.

The treatment blocks formed from the solid block composition may be used with or without an ancillary device or structure. In one manner of use one or more treatment blocks are supplied to the cistern of a toilet where they sink and typically rest upon the bottom until they are consumed. In another manner of use one or more treatment blocks are supplied to the interior of a sanitary appliance, e.g., a toilet bowl or interior of a urinal wherein the treatment block(s) are within the path of flush water flushed through the sanitary appliance during its normal manner of use.

According to certain preferred embodiments the solid block compositions are used with a device such as a container which is suspended upon the rim of a toilet bowl and which permits for the passage of flush water through the container and into the toilet bowl.

The manufacture of the solid treatment blocks from the solid block composition according to the present invention is well within the capability of persons of ordinary skill in the art. Exemplary useful processes contemplate by mixing the included constituents into a homogeneous mass and noodling, plodding, extruding, cutting and stamping the mass to form uniform bars or cakes. The constituents ultimately present in the solid blocks are preferably formed by tabletting, casting or extrusion using known techniques. Most preferably solid blocks are conveniently and preferably made by extrusion. Usually all of the solid ingredients are mixed in any suitable blending equipment followed by the addition of liquid ingredients under blending conditions. The resulting homogeneous blend is then extruded.

The blocks of the invention may be conveniently formed by a compression process, especially an extrusion process comprising the steps of forming a mixture of the components of the composition, extruding this mixture into rod or bar form and then cutting the extruded rod or bar into appropriately sized pieces or blocks. Typically, the treatment blocks of the present invention weigh from 25 to 250 grams, preferably from about 20 to about 90 grams. The blocks are typically cylindrical, square or rectangular in shape or cross-section, and desirably have a high ratio of surface area to block volume.

Particularly preferred compositions exhibit a long service life, and additionally exhibit a high ratio of surface area to block volume, preferably wherein the ratio of block volume to block surface area is at least about 0.25, preferably at least about 0.27, more preferably is at least about 0.30. Notwithstanding the relatively high surface area to volume ratio (e.g., $cm^2/cm^3$, $mm^2/mm^3$, $in^2/in^3$) particularly preferred embodiments of the invention provide a long service life in use, particularly when used in an ITB device which subjects the blocks to flushing water, which is surprising in view of known art block compositions used in ITB devices. Such is further surprising in view of the lesser amounts of essential anionic surfactants present in preferred embodiments of the treatment blocks when compared to many prior art treatment block compositions.

In order to further illustrate the present invention, various examples including preferred embodiments of the invention are described amongst the examples. In these examples, as well as throughout the balance of this specification and claims, all parts and percentages are by weight unless otherwise indicated.

EXAMPLES

Blocks having the compositions on the following table were produced by extruding the constituents into blocks having a size of 20 mm by 10 mm by 75 mm, which provides a block having surface area/volume ratio of 4500 mm2/15000 mm3, or 0.3. Each of the constituents were provided in the weigh percentages set forth on Table 1, and unless otherwise indicated, are considered to be 100% wt. active.

TABLE 1

|  | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|
| dodecylbenzene sulfonate, sodium salt (80%) | 27.0 | 22.0 | 32.0 | 35.00 | 37.8 | 32.0 | 35.0 | 37.0 | 32.0 |
| sodium C14/C16 olefin sulfonates (80%) | 15.0 | 20.0 | 15.0 | 22.0 | 23.62 | 20.0 | 22.0 | 25.0 | 20.0 |
| silica | 2.0 | 2.0 | 2.0 | 2.0 | 1.89 | 2.0 | 2.0 | 2.0 | 2.0 |
| lauramide monoethanol amide (98%) | 30.0 | 30.0 | 25.0 | 15.00 | 12.28 | 20.0 | 15.0 | 10.0 | 20.0 |
| sodium sulfate | 20.5 | 20.5 | 20.5 | 20.50 | 18.90 | 20.5 | 20.5 | 20.5 | 18.5 |
| dichlorocyanurate dihydrate, sodium salt (56% bleach) | 2.5 | 2.5 | 2.5 | 2.4 | 2.41 | 2.5 | 2.5 | 2.5 | 2.5 |
| paraffinic hydrocarbons | 3.0 | 3.0 | 3.0 | 3.1 | 3.09 | 3.0 | 3 | 3 | 5 |

The identity of the constituents used to form the treatment blocks are identified more specifically on the following Table 2.

TABLE 2

| dodecylbenzene sulfonate, sodium salt (80%) | anionic surfactant, dodecylbenzene sulfonate, 80% wt. actives |
| sodium C14/C16 olefin sulfonates (80%) | anionic surfactant, sodium C14/C16 olefin sulfonates, 80% wt. actives |
| silica | filler anhydrous silica, 100% wt. actives. |
| lauramide monoethanol amide (98%) | solubility control agent, lauramide monoethanol amide, 98% wt. actives |
| sodium sulfate | diluent, sodium sulfate, 100% wt. actives |
| dichlorocyanurate dihydrate, sodium salt (56%) | bleach constituent, dichlorocyanurate dihydrate, sodium salt, 56% wt. bleach actives |
| Isopar M | hydrocarbon solvent, isoparaffinic organic solvents, 100% wt. actives |
| mineral oil | Hydrocarbon solvent, mineral oil, 100% wt. actives |
| paraffinic hydrocarbons | Hydrocarbon solvent, white paraffin oil, 100% wt. actives |

All of the anhydrous constituents, excluding the bleach constituent are dry blended to form a premixture, which is subsequently metered concurrently with appropriate metered amounts of the bleach constituent into the throat of a twin-screw extruder. The twin-screw extruder is operated at low temperatures and pressures, and during mixing metered amounts of the hydrocarbon solvent constituent is injected into the extruder barrel at a port located about one-third of the distance of the length of the extruder barrel downstream of the throat. The twin-screw extruder is used to form a homogeneous blend of the solid block constituents. Subsequently the exiting homogenous blend exiting the twin-screw extruder is supplied to the throat of s single screw extruder which is used to compress the homogenous blend into a solid mass.

The treatment blocks exhibit good dimensional stability both after manufacture and prior to use in the cleaning treatment of a sanitary appliance, e.g., a toilet or urinal, as well as during the cleaning treatment of a sanitary appliance.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

The invention claimed is:

1. A solid treatment block formed from a solid block composition which comprises:
    10-40% wt. of a linear alkyl benzene sulfonate surfactant;
    8-40% wt. of an alpha olefin sulfonate anionic surfactant;
    10-40% wt. of one or more mono- or di-alkanol amides derived from $C_8$-$C_{16}$ fatty acids
    5-30% wt. of a diluent material;
    0.1-15% wt. of a filler material;
    0.05-7% wt. of a bleach constituent;
    at least 0.1% wt. of a paraffinic hydrocarbon constituent;
    further optionally to 40% wt. further additive constituents.

2. A solid treatment block formed from a solid block composition according to claim 1 wherein the linear alkyl benzene sulfonate surfactants and the alpha olefin sulfonate anionic surfactant are the sole anionic surfactants present in the solid treatment block composition.

3. A solid treatment block formed from a solid block composition according to claim 1 which includes at least one further cosurfactant selected from further anionic, nonionic, cationic, amphoteric, and zwitterionic surfactants.

4. A solid treatment block formed from a solid block composition according to claim 1 wherein the ratio of block volume to block surface area is at least about 0.25.

5. A solid treatment block formed from a solid block composition according to claim 4 wherein the ratio of block volume to block surface area is at least about 0.27.

6. A solid treatment block formed from a solid block composition according to claim 4 wherein the ratio of block volume to block surface area is at least about 0.30.

7. A solid treatment block according to claim 1 wherein the block composition loses not more than 50% of its initial weight subsequent to 100 flush cycles when the block has been suspended in an ITB device in the path of flush water released from the cistern during each flush cycle.

8. A solid treatment block according claim 7 wherein the block composition loses not more than 20% of its initial weight subsequent to 100 flush cycles when the block has been suspended in an ITB device in the path of flush water released from the cistern during each flush cycle.

9. A solid treatment block according claim 8 wherein the block composition loses not more than 10% of its initial weight subsequent to 100 flush cycles when the block has been suspended in an ITB device in the path of flush water released from the cistern during each flush cycle.

10. A solid treatment block according to claim 1 formed from a solid block composition which comprises:
    15-35% wt of a linear alkyl benzene sulfonate surfactant.

11. A solid treatment block according to claim 1 formed from a solid block composition which comprises:
    9-35% wt. of an alpha olefin sulfonate anionic surfactant.

12. A solid treatment block according to claim 1 formed from a solid block composition which comprises:
    10-35% wt. of one or more mono- or di-alkanol amides derived from $C_8$-$C_{16}$ fatty acids.

13. A solid treatment block according to claim 1 formed from a solid block composition which comprises:
    15-25% wt. of a diluent material.

14. A solid treatment block according to claim 1 formed from a solid block composition which comprises:
    0.5-5% wt. of a filler material.

15. A solid treatment block according to claim 1 formed from a solid block composition which comprises:
    1-3.5% wt. of a bleach constituent.

16. A solid treatment block according to claim 1 formed from a solid block composition wherein:
    the one or more mono- or di-alkanol amides derived from $C_8$-$C_{16}$ fatty acids are $C_{12}$-$C_{14}$ fatty acids having a $C_2$-$C_6$ monoamine or diamine moiety.

17. A solid treatment block according to claim 1 formed from a solid block composition wherein:
    the one or more mono- or di-alkanol amides derived from $C_8$-$C_{16}$ fatty acids are $C_{12}$-$C_{14}$ fatty acids are a linear $C_2$-$C_6$ monoethanol amide.

18. A solid treatment block according to claim 1, wherein:
    alcohols are absent from the solid treatment block composition.

19. A solid treatment block according to claim 1, wherein the paraffinic hydrocarbon is selected from the group consisting of: $C_7$-$C_8$ isoparaffins, $C_{10}$-$C_{11}$ isoparaffins, $C_{11}$-$C_{12}$ isoparaffins, $C_{11}$-$C_{13}$ isoparaffins, $C_{13}$-$C_{14}$ isoparaffins and $C_{12}$-$C_{20}$ isoparaffins.

20. A solid treatment block according to claim 1, wherein the paraffinic hydrocarbon is selected from the group consisting of: linear or branched, saturated or unsaturated hydrocarbons having from about 6 to about 24 carbon atoms.

21. A solid treatment block according to claim 1, comprising 2-10% wt. of a paraffinic hydrocarbon.

* * * * *